(12) United States Patent
Gruver et al.

(10) Patent No.: US 8,637,739 B2
(45) Date of Patent: Jan. 28, 2014

(54) ANTI-NEMATODE PEPTIDES AND METHODS OF USE THEREOF

(75) Inventors: Steven D. Gruver, Pacifica, CA (US); Lu Liu, Palo Alto, CA (US); Ute Schellenberger, Palo Alto, CA (US); Jun-Zhi Wei, Palo Alto, CA (US); Wieping Xie, East Palo Alto, CA (US); Genhai Zhu, San Jose, CA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/541,202

(22) Filed: Jul. 3, 2012

(65) Prior Publication Data

US 2013/0031667 A1    Jan. 31, 2013

Related U.S. Application Data

(60) Provisional application No. 61/512,743, filed on Jul. 28, 2011.

(51) Int. Cl.
*A01H 5/00* (2006.01)
*A01H 1/00* (2006.01)
*C12N 15/00* (2006.01)
*C12N 15/82* (2006.01)

(52) U.S. Cl.
USPC ........ 800/301; 800/279; 800/302; 435/320.1; 435/468; 536/23.2

(58) Field of Classification Search
None
See application file for complete search history.

(56) References Cited

PUBLICATIONS

NCBI. 2010. Sphingobacterium spiritivorum ATCC 33861 Contig 332, whole genome shotgun sequence. protein ID EFK55868.1. GenBank: ACHA02000012.1. p. 1-2.*
Guo et al. 2004. Protein tolerance to random amino acid change. PNAS. 101(25):9205-9210.*

* cited by examiner

*Primary Examiner* — Anne Kubelik
*Assistant Examiner* — Jeffrey Bolland

(57) ABSTRACT

The invention provides novel polypeptides, and variants and fragments thereof, having pesticidal activity against nematodes. Particular embodiments of the invention provide isolated nucleic acids encoding pesticidal proteins, biopesticide compositions, expression cassettes, and transformed microorganisms and plants comprising a nucleic acid of the invention. These compositions find use in methods for controlling pests, especially plant parasitic nematodes.

19 Claims, 3 Drawing Sheets

Figure 1a

MHRREALQRV ALLMGGTVIG ANLFLEGCSR SASKDTAKLF EKDSVNFLGD LAEAILPKTS TPGAKEAGVG
EFIPVMIRDC YADTEQKVFL DGINTVDERA KKEFGKKFQE LSKEDQTKFV NILDKEASEY NAKQAEATKA
QREKDALKQN EMYRVPKSDP PHWFTMFKQL TLTGFFTSEL GATKALRYVK IPGKFDGNYP YKKGEHAWA
(SEQ ID NO:1)

Figure 1b

ATGCATAGAAGAGAA GCATTACAGCGTGTC GCCCTGTTGATGGGA GGAACTGTCATTGGC
GCTAATCTTTTCCTG GAAGGCTGTTCACGT TCAGCTTCAAAAGAT ACAGCAAAACTTTTT
GAAAAGATTCGGTC AATTTTCTTGGCGAT CTGGCAGAAGCGATC TTGCCCAAAACAAGT
ACACCGGGAGCGAAG GAAGCAGGCGTAGGA GAATTTATCCCTGTC ATGATCAGAGACTGT
TATGCAGACACTGAG CAAAAGGTATTCTTA GACGGAATCAATACT GTTGATGAACGTGCT
AAGAAGGAATTCGGT AAGAAGTTTCAGGAA CTAAGTAAGGAAGAT CAGACTAAATTTGTC
AATATTCTTGATAAA GAAGCCAGTGAATAC AACGCTAAGCAGGCA GAAGCTACAAAAGCA
CAGCGTGAAAAGGAT GCATTGAAACAAAAT GAAATGTATCGTGTG CCGAAAAGCGATCCG
CCACACTGGTTCACG ATGTTCAAGCAATTG ACCCTTACAGGTTTC TTTACTTCAGAACTG
GGCGCTACTAAAGCG CTACGTTATGTGAAA ATTCCGGGGAAATTT GATGGTAATTATCCT
TATAAAAAAGGAGAG CACGCCTGGGCATAA (SEQ ID NO:2)

Figure 2a

MNRREALQRV ALLMGGTVIG ANLFLEGCSR SASKDTAKLF EKDSVNFLGD LAEAILPKTS TPGAKEAGVG
EFIPVMIRDC YADTEQKVFL DGINTVDERA KKEFGKKFQE LSKEDQTKFV NILDKEASEY NAKQAEATKA
QREKDALKQN EMYRVPKSDP PHWFTMFKQL TLTGFFTSEL GATKALRYVK IPGKFDGNYP YKKGEHAWA
(SEQ ID NO:3)

Figure 2b

ATGAATAGAAGAGAA GCATTACAGCGTGTC GCCCTGTTGATGGGA GGAACTGTCATTGGC
GCTAATCTTTTCCTG GAAGGCTGTTCACGT TCAGCTTCAAAAGAT ACAGCAAAACTTTTT
GAAAAAGATTCGGTC AATTTTCTTGGCGAT CTGGCAGAAGCGATC TTGCCCAAAACAAGT
ACACCGGGAGCGAAG GAAGCAGGCGTAGGA GAATTTATCCCTGTC ATGATCAGAGACTGT
TATGCAGACACTGAG CAAAAGGTATTCTTA GACGGAATCAATACT GTTGATGAACGTGCT
AAGAAGGAATTCGGT AAGAAGTTTCAGGAA CTAAGTAAGGAAGAT CAGACTAAATTTGTC
AATATTCTTGATAAA GAAGCCAGTGAATAC AACGCTAAGCAGGCA GAAGCTACAAAAGCA
CAGCGTGAAAAGGAT GCATTGAAACAAAAT GAAATGTATCGTGTG CCGAAAAGCGATCCG
CCACACTGGTTCACG ATGTTCAAGCAATTG ACCCTTACAGGTTTC TTTACTTCAGAACTG
GGCGCTACTAAAGCG CTACGTTATGTGAAA ATTCCGGGGAAATTT GATGGTAATTATCCT
TATAAAAAAGGAGAG CACGCCTGGGCAT (SEQ ID NO:4)

ANTI-NEMATODE PEPTIDES AND METHODS OF USE THEREOF

CROSS-REFERENCE TO RELATED APPLICATIONS

This application claims priority to U.S. Provisional Application No. 61/512,743, filed Jul. 28, 2011, which is hereby incorporated herein in its entirety by reference.

FIELD OF THE INVENTION

The present invention relates to polypeptides having pesticidal, particularly nematicidal, activity and polynucleotides that encode the same. Methods of the invention utilize these pesticidal polynucleotides and polypeptides to control plant pests and to increase pest resistance in plants.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 394049SEQLIST.txt, created on Jul. 28, 2011, and having a size of 6 kilobytes and is filed concurrently with the specification. The sequence listing contained in this ASCII formatted document is part of the specification and is herein incorporated by reference in its entirety.

BACKGROUND OF THE INVENTION

Plant pests, including plant-parasitic nematodes, are a major factor in the loss of the world's agricultural crops. Agriculturally significant nematodes include the sedentary endoparasites, such as those found in the genera *Meloidogyne* (root-knot nematodes), *Heterodera*, and *Globedera* (cyst nematodes).

Currently, plant-parasitic nematodes are generally controlled by chemical nematicides, crop rotation, and growing resistant cultivars. The use of chemical nematicides, however, increases costs to farmers and can cause harmful effects on the ecosystem. Moreover, consumers and government regulators alike are becoming increasingly concerned with the environmental hazards associated with the production and use of synthetic agrochemicals. Traditional breeding methods can be used to select resistant cultivars, but the methods are time-consuming and require continuous effort to maintain disease resistance. See, for example, Grover and Gowthaman (2003) *Curr. Sci.* 84:330-340. Thus, there is substantial interest in developing novel alternatives for the control of plant pathogens that possess a lower risk of pollution and environmental hazards than is characteristic of traditional agrochemical-based methods and that are less cumbersome than conventional breeding techniques.

A number of biotechnology-based strategies, including disruption of the feeding structure of the nematodes by localized expression of phytotoxic gene product(s) have been investigated, but none of them has reached commercial success. Nevertheless, biological control of plant pests of agricultural significance using a microbial agent, such as proteins derived from fungi, bacteria, or insects, affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops. Thus, there remains a need for biopesticides having nematicidal activity and methods of using such biopesticides to protect crops from plant-parasitic nematodes.

BRIEF SUMMARY OF THE INVENTION

Compositions and methods for protecting a plant from a pest are provided. The compositions comprise polypeptides comprising putative twin-arginine translocation signal peptides and displaying pesticidal activity against nematodes, including plant-parasitic nematodes. Polynucleotides comprising nucleotide sequences that encode the presently disclosed polypeptides are further provided. Compositions also include expression cassettes comprising a polynucleotide that encodes a polypeptide disclosed herein. Plants, plant cells, seeds, and microorganisms comprising the presently disclosed polynucleotides and polypeptides are further provided.

The compositions are useful in methods directed to inducing pest resistance, particularly plant-parasitic nematode resistance in plants. In particular embodiments, the methods comprise introducing into a plant at least one polynucleotide that encodes a pesticidal (e.g., nematicidal) polypeptide of the invention. As a result, the pesticidal polypeptide is expressed in the plant, and the pest (e.g., plant parasitic nematode) is exposed to the preferred protein at the site of attack, thereby leading to increased pest resistance. A tissue-preferred promoter may be used to drive expression of a pesticidal protein of the invention in specific plant tissues that are particularly vulnerable to pest attack. For control of nematodes, a root preferred promoter may be used.

Further provided are biopesticide compositions and formulations and methods for their use in protecting a plant from a pest, particularly a plant-parasitic nematode. In some embodiments, the compositions comprise a carrier in combination with a pesticidal (e.g., nematicidal) polypeptide of the invention or a microorganism comprising a polynucleotide that encodes a pesticidal (e.g., nematicidal) polypeptide of the invention. Methods of using these compositions to protect a plant from a pest comprise applying the biopesticide composition to the environment of a plant pest by, for example, spraying, dusting, broadcasting, or seed coating.

The following embodiments are encompassed by the present invention:

1. An isolated polypeptide comprising an amino acid sequence selected from the group consisting of:
   (a) the amino acid sequence set forth in SEQ ID NO: 1; and,
   (b) an amino acid sequence having at least 90% sequence identity to SEQ ID NO: 1, wherein said amino acid sequence is not SEQ ID NO: 3, and wherein said polypeptide has nematicidal activity.

2. The isolated polypeptide of embodiment 1, wherein said polypeptide has nematicidal activity against a nematode that is a member of a *Meloidogyne*, *Heterodera*, or *Globedera* genera.

3. An isolated polynucleotide comprising a nucleotide sequence selected from the group consisting of:
   (a) the nucleotide sequence set forth in SEQ ID NO: 2;
   (b) a nucleotide sequence encoding an amino acid sequence comprising SEQ ID NO: 1;
   (c) a nucleotide sequence having at least 90% sequence identity to SEQ ID NO: 2, wherein said polynucleotide encodes a polypeptide having nematicidal activity, and wherein said polypeptide does not have the amino acid sequence set forth in SEQ ID NO: 3; and, (d) a nucleotide sequence encoding an amino acid sequence having at least 90% sequence identity to SEQ ID NO: 1, wherein said amino acid sequence is not SEQ ID NO: 3, and wherein said polynucleotide encodes a polypeptide having nematicidal activity.

4. The isolated polynucleotide of embodiment 3, wherein said polynucleotide encodes a polypeptide having nematicidal activity against a nematode that is a member of a *Meloidogyne, Heterodera*, or *Globedera* genera.

5. An expression cassette comprising a nucleotide sequence selected from the group consisting of:
   (a) the nucleotide sequence set forth in SEQ ID NO: 2;
   (b) a nucleotide sequence encoding an amino acid sequence comprising SEQ ID NO: 1;
   (c) a nucleotide sequence having at least 90% sequence identity to SEQ ID NO: 2, wherein said nucleotide sequence encodes a polypeptide having nematicidal activity; and,
   (d) a nucleotide sequence encoding an amino acid sequence having at least 90% sequence identity to SEQ ID NO: 1, wherein said nucleotide sequence encodes a polypeptide having nematicidal activity.

6. The expression cassette of embodiment 5, wherein said nucleotide sequence encodes a polypeptide having an amino acid sequence that differs from the amino acid sequence set forth in SEQ ID NO: 3.

7. The expression cassette of embodiment 5, wherein said nucleotide sequence is operably linked to a promoter that drives expression in a plant.

8. The expression cassette of embodiment 5, wherein said nucleotide sequence is operably linked to a promoter that drives expression in a microorganism.

9. A host cell comprising a nucleotide sequence selected from the group consisting of:
   (a) the nucleotide sequence set forth in SEQ ID NO: 2;
   (b) a nucleotide sequence encoding an amino acid sequence comprising SEQ ID NO: 1;
   (c) a nucleotide sequence having at least 90% sequence identity to SEQ ID NO: 2, wherein said nucleotide sequence encodes a polypeptide having nematicidal activity; and,
   (d) a nucleotide sequence encoding an amino acid sequence having at least 90% sequence identity to SEQ ID NO: 1, wherein said nucleotide sequence encodes a polypeptide having nematicidal activity.

10. The host cell of embodiment 9, wherein said nucleotide sequence encodes a polypeptide having an amino acid sequence that differs from the amino acid sequence set forth in SEQ ID NO: 3.

11. A host cell comprising the expression cassette of embodiment 7 or 8.

12. A plant comprising a heterologous polynucleotide operably linked to a promoter that drives expression in the plant, wherein said heterologous polynucleotide comprises a nucleotide sequence selected from the group consisting of:
   (a) the nucleotide sequence set forth in SEQ ID NO: 2;
   (b) a nucleotide sequence encoding an amino acid sequence comprising SEQ ID NO: 1;
   (c) a nucleotide sequence having at least 90% sequence identity to SEQ ID NO: 2, wherein said heterologous polynucleotide encodes a polypeptide having nematicidal activity; and,
   (d) a nucleotide sequence encoding an amino acid sequence having at least 90% sequence identity to SEQ ID NO: 1, wherein said heterologous polynucleotide encodes a polypeptide having nematicidal activity.

13. The plant of embodiment 12, wherein said nucleotide sequence encodes a polypeptide having an amino acid sequence that differs from the amino acid sequence set forth in SEQ ID NO: 3.

14. The plant of embodiment 12, wherein said heterologous polynucleotide encodes a polypeptide having nematicidal activity against a nematode that is a member of a *Meloidogyne, Heterodera*, or *Globedera* genera.

15. The plant of embodiment 12, wherein said promoter is a root-preferred promoter.

16. The plant of embodiment 12, wherein said plant is a monocot.

17. The plant of embodiment 16, wherein said monocot is maize, sugarcane, wheat, rice, barley, sorghum, or rye.

18. The plant of embodiment 12, wherein said plant is a dicot.

19. The plant of embodiment 18, wherein said dicot is soybean, *Brassica*, sunflower, cotton, alfalfa, or tomato.

20. A transformed seed of the plant of any one of embodiments 12-19.

21. A method of enhancing pest resistance in a plant, said method comprising providing to said plant a polypeptide comprising an amino acid sequence selected from the group consisting of:
   (a) the amino acid sequence set forth in SEQ ID NO: 1; and,
   (b) an amino acid sequence having at least 90% sequence identity to SEQ ID NO: 1, wherein said polypeptide has nematicidal activity.

22. The method of embodiment 21, wherein said amino acid sequence is not SEQ ID NO: 3.

23. The method of embodiment 21, wherein said polypeptide has nematicidal activity against a nematode that is a member of a *Meloidogyne, Heterodera*, or *Globedera* genera.

24. The method of embodiment 21, wherein said plant is planted in an area of cultivation, wherein said area of cultivation comprises said pest, or wherein environmental conditions in said area of cultivation are conducive to the growth of said pest.

25. The method of embodiment 21, wherein providing the polypeptide comprises introducing into said plant a heterologous polynucleotide comprising a nucleotide sequence selected from the group consisting of:
   (a) the nucleotide sequence set forth in SEQ ID NO: 2;
   (b) a nucleotide sequence encoding the amino acid sequence comprising SEQ ID NO: 1;
   (c) a nucleotide sequence having at least 90% sequence identity to SEQ ID NO: 2, wherein said polynucleotide encodes a polypeptide having nematicidal activity; and,
   (d) a nucleotide sequence encoding an amino acid sequence having at least 90% sequence identity to SEQ ID NO: 1, wherein said polynucleotide encodes a polypeptide having nematicidal activity.

26. The method of embodiment 25, wherein said nucleotide sequence encodes a polypeptide having an amino acid sequence that differs from the amino acid sequence set forth in SEQ ID NO: 3.

27. The method of embodiment 25, wherein said heterologous polynucleotide encodes a polypeptide having nematicidal activity against a nematode that is a member of a *Meloidogyne, Heterodera*, or *Globedera* genera.

28. The method of embodiment 25, wherein said heterologous polynucleotide is stably integrated into the genome of the plant.

29. The method of embodiment 25, wherein said heterologous polynucleotide is operably linked to a promoter active in said plant.

30. The method of embodiment 29, wherein said promoter is a tissue-preferred promoter.

31. The method of embodiment 30, wherein said tissue-preferred promoter is a root-preferred promoter.

32. A biopesticide composition comprising at least one polypeptide, wherein said polypeptide comprises an amino acid sequence selected from the group consisting of:

(a) the amino acid sequence set forth in SEQ ID NO: 1; and, (b) an amino acid sequence having at least 90% sequence identity to SEQ ID NO: 1, wherein said polypeptide has nematicidal activity.

33. The biopesticide composition of embodiment 32, wherein said amino acid sequence is not SEQ ID NO: 3.

34. The biopesticide composition of embodiment 32 further comprising a carrier.

35. A method for protecting a plant from a plant pest comprising applying the biopesticide composition according to embodiment 32 to the environment of a plant pest.

36. The method of embodiment 35, wherein said biopesticide composition is applied by a procedure selected from the group consisting of spraying, dusting, broadcasting, and seed coating.

37. The method of embodiment 35, wherein said plant pest is a nematode.

38. The method of embodiment 37, wherein said nematode is a member of a *Meloidogyne, Heterodera*, or *Globedera* genera.

39. A biopesticide composition comprising a microorganism, wherein said microorganism comprises at least one heterologous polynucleotide operably linked to a promoter that drives expression in the microorganism, wherein said heterologous polynucleotide comprises a nucleotide sequence selected from the group consisting of:

(a) the nucleotide sequence set forth in SEQ ID NO: 2;

(b) a nucleotide sequence encoding the amino acid sequence comprising SEQ ID NO: 1;

(c) a nucleotide sequence having at least 90% sequence identity to SEQ ID NO: 2, wherein said heterologous polynucleotide encodes a polypeptide having nematicidal activity; and, (d) a nucleotide sequence encoding an amino acid sequence having at least 90% sequence identity to SEQ ID NO: 1, wherein said heterologous polynucleotide encodes a polypeptide having nematicidal activity.

40. The biopesticide composition of embodiment 39, wherein said nucleotide sequence encodes a polypeptide having an amino acid sequence that differs from the amino acid sequence set forth in SEQ ID NO: 3.

41. The biopesticide composition of embodiment 39, wherein said heterologous polynucleotide encodes a polypeptide having nematicidal activity against a nematode that is a member of a *Meloidogyne, Heterodera*, or *Globedera* genera.

42. The biopesticide composition of embodiment 39 further comprising a carrier.

43. A method for protecting a plant from a pest comprising applying the biopesticide composition according to embodiment 39 to the environment of a plant pest.

44. The method of embodiment 43, wherein said biopesticide composition is applied by a procedure selected from the group consisting of spraying, dusting, broadcasting, and seed coating.

45. The method of embodiment 43, wherein said plant pest is a nematode.

46. The method of embodiment 45, wherein said nematode is a member of a *Meloidogyne, Heterodera*, or *Globedera* genera.

47. A method for controlling a pest in an area of cultivation, said method comprising:

a) evaluating environmental conditions in an area of cultivation for the presence of a pest or conditions conducive to the growth of a pest;

b) selecting an effective amount of a biopesticide composition, wherein the biopesticide composition is the biopesticide composition according to embodiment 32 or embodiment 39; and c) applying said biopesticide composition to a crop, crop part, seed, or an area of cultivation of said crop.

48. A method for controlling a pest in an area of cultivation, said method comprising:

a) evaluating environmental conditions in an area of cultivation for the presence of a pest or conditions conducive to the growth of a pest; and b) planting the area with crop seeds or plants comprising a heterologous polynucleotide operably linked to a promoter that drives expression in the plant, wherein said heterologous polynucleotide comprises a nucleotide sequence selected from the group consisting of:

(i) the nucleotide sequence set forth in SEQ ID NO: 2;

(ii) a nucleotide sequence encoding the amino acid sequence comprising SEQ ID NO: 1;

(iii) a nucleotide sequence having at least 90% sequence identity to SEQ ID NO: 2, wherein said heterologous polynucleotide encodes a polypeptide having nematicidal activity; and, (iv) a nucleotide sequence encoding an amino acid sequence having at least 90% sequence identity to SEQ ID NO: 1, wherein said heterologous polynucleotide encodes a polypeptide having nematicidal activity.

49. The method of embodiment 48, wherein said nucleotide sequence encodes a polypeptide having an amino acid sequence that differs from the amino acid sequence set forth in SEQ ID NO: 3.

50. The method of embodiment 47 or 48, wherein said pest is a nematode.

51. The method of embodiment 50, wherein said nematode is a member of a *Meloidogyne, Heterodera*, or *Globedera* genera.

These and other aspects of the invention are disclosed in more detail in the description of the invention given below.

BRIEF DESCRIPTION OF THE FIGURES

FIGS. 1A and 1B depict the amino acid and nucleic acid coding sequences, respectively, for RX025, a novel *Sphingobacterium spiritivorum* protein isolated from strain 75G5.

Figure 3:
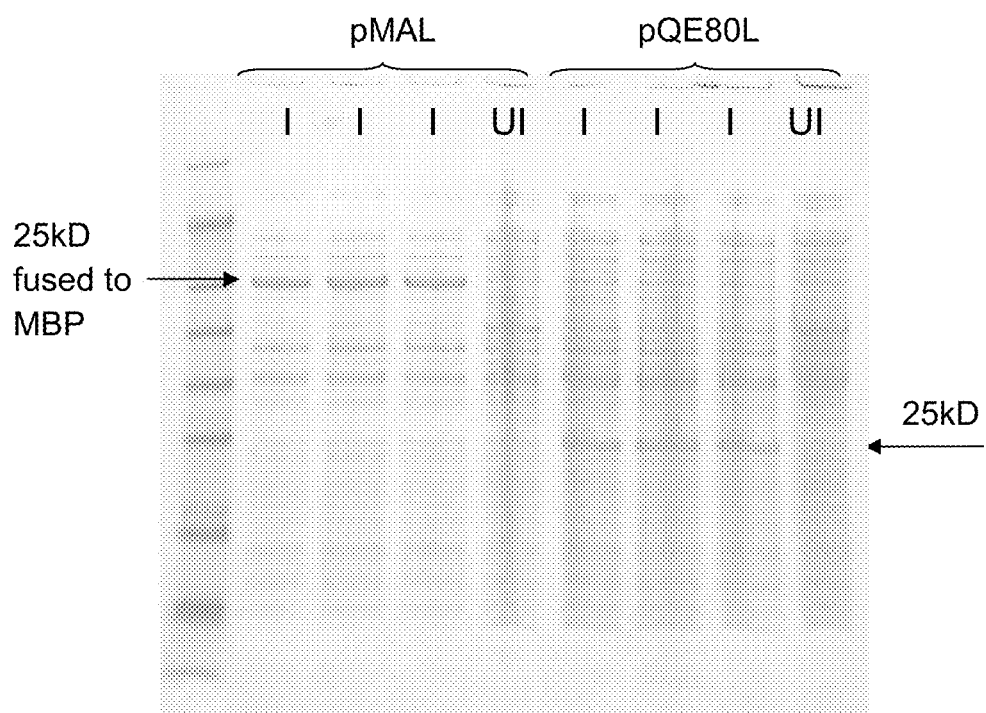

FIGS. 2A and 2B depict the amino acid sequence of SEQ ID NO: 3 and the nucleic acid sequence of SEQ ID NO: 4, respectively. The sequences are closely related to RX025, but have previously unknown function.

FIG. 3 depicts a protein gel showing total protein from *E. coli* strains that have been transformed with a vector (pMAL or pQE80L) that comprises the RX025 gene. "I" indicates lanes in which expression of the RX025 gene has been induced; "UI" refers to lanes in which the cells were uninduced.

DETAILED DESCRIPTION OF THE INVENTION

The present invention is based, in part, on the discovery and isolation of a novel *Sphingobacterium spiritivorum* protein. The novel proteins of the invention comprise putative twin-arginine translocation signal peptides and display pesticidal activity against nematodes. Accordingly, the invention provides isolated polypeptides (e.g., peticidal polypeptides, particularly nematicidal polypeptides), isolated polynucleotides that encode such polypeptides, and expression cassettes comprising the presently disclosed polynucleotides. Biopesticide compositions are also disclosed. Such compositions may comprise a presently disclosed polypeptide optionally in combination with a carrier or a transformed microorganism that expresses a polypeptide of the invention.

Compositions of the invention include isolated polypeptides having the sequence set forth in SEQ ID NO: 1, and variants and fragments thereof. Additional compositions include isolated polynucleotides comprising the sequence set forth in SEQ ID NO: 2, nucleotide sequences that encode the amino acid sequence of SEQ ID NO: 1, and variants and fragments thereof. In certain embodiments, the polynucleotides of the invention have been optimized for expression by the cells of a particular organism, e.g., nucleic acid sequences that have been back-translated (i.e., reverse translated) using plant-preferred codons based on the amino acid sequence of a polypeptide of the invention (e.g., a polypeptide having pesticidal activity).

The nucleic acids and nucleotide sequences of the invention may be used to transform an organism needing protection from an insect or nematode pest to produce the encoded polypeptides. Accordingly, the invention further provides transgenic organisms (e.g., transgenic plants and microorganisms) comprising heterologous polynucleotides that encode polypeptides of the invention (e.g., pesticidal polypeptides). Methods are provided that involve the use of such transformed organisms to impact or control pests, particularly plant pests, more particularly nematodes.

Thus, the invention involves the discovery of biodegradable pesticides and the genes that encode them, thereby providing new approaches for impacting plant pests that do not depend on the use of traditional, synthetic chemicals. As used herein, the term "plant pest" refers to any organism that can cause harm to a plant by inhibiting or slowing the growth of a plant, by damaging the tissues of a plant, by weakening the immune system of a plant, reducing the resistance of a plant to abiotic stresses, and/or by causing the premature death of the plant, etc. Relevant plant pests include, e.g., nematodes, insects, and the like.

As used herein, the term "impacting pests" refers to effecting changes in pest feeding, growth, and/or behavior at any stage of development, including but not limited to: killing the pest; retarding its growth; preventing or reducing its reproductive capability; preventing or reducing its ability to feed; and the like.

As used herein, the term "pesticidal activity" refers to the activity of an organism or a substance (such as, for example, a protein) that can be measured by, e.g., pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. "Pesticidal proteins" are proteins that display pesticidal activity by themselves or in combination with other proteins.

In particular embodiments, the pesticidal activity exhibited by the polypeptides of the invention is nematicidal activity. As used herein, "nematicidal activity" refers to the ability to adversely impact at least one measurable parameter of nematode fitness. In certain embodiments, the nematicidal activity is measured with respect to a nematode that is a member of a *Meloidogyne*, *Heterodera*, or *Globedera* genera. In other embodiments, the nematicidal activity is measured with respect to a nematode that is selected from the group consisting of *Panagrellus redivivus*, *Distolabrellus veechi*, *Nippostrongylus brasiliensis*, and *Caenorhabditis elegans*. Evidence of nematicidal activity includes, for example, lack of pumping, inhibition of growth (i.e., small size), pale coloration, lethargy, decreased reproduction, and/or death. See, e.g., Wei et al. (2003), Proc. Nat'l Acad. Sci. 100(5):2760-65.

In other embodiments, the pesticidal activity exhibited by the polypeptides of the invention is insecticidal activity. As used herein, "insecticidal activity" refers to the ability to adversely impact insect growth or reproduction, or to kill the insect. Insecticidal activity can be measured by insect assays.

As used herein, the term "pesticidally effective amount" connotes a quantity of a substance or organism that has pesticidal activity when present in the environment of a pest. For each substance or organism, the pesticidally effective amount is determined empirically for each pest affected in a specific environment. A "nematicidally effective amount" may be used to refer to a "pesticidally effective amount" when the pest is a nematode. Similarly, an "insecticidally effective amount" may be used to refer to a "pesticidally effective amount" when the pest is an insect pest.

As used herein, the term "plant" also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

As used herein, the terms "encoding" or "encoded" when used in the context of a specified polynucleotide mean that the polynucleotide comprises the requisite information to direct translation of the nucleotide sequence into a specified protein. The information by which a protein is encoded is specified by the use of codons. A polynucleotide encoding a protein may comprise non-translated sequences (e.g., introns) within translated regions of the polynucleotide or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the presently disclosed pesticidal proteins or biologically active portions thereof are recombinantly produced, optimally culture medium represents less than about 30%, about 20%, about 10%, about 5%, or about 1% (by dry weight) of chemical precursors or non-protein-of-interest chemicals.

Fragments and variants of the disclosed polypeptides and polynucleotides encoding such polypeptides are also encompassed by the present invention. By "fragment" is intended a portion of the amino acid sequence of the disclosed polypeptide (i.e., a portion of the sequence of SEQ ID NO: 1) or a portion of the nucleic acid sequence of a polynucleotide encoding such a polypeptide (e.g., a portion of the sequence of SEQ ID NO: 2). Fragments of interest include those that retain pesticidal activity. For example, in certain embodiments, the polypeptide fragment is a fragment of SEQ ID NO: 1 that lacks about 1, about 2, about 3, about 4, about 5, about 10, about 15, about 20, about 25, about 30, about 35, about 40, about 45, about 50, or more amino acids from the C-terminus. In certain embodiments, the polypeptide fragment comprises a twin-arginine translocation signal peptide.

A polynucleotide fragment of the invention may encode a biologically active portion of a polypeptide of the invention, or it may be a fragment that can be used as a hybridization probe or PCR primer using methods disclosed below. A biologically active portion of a polypeptide of the invention can be a polypeptide fragment disclosed herein (e.g., a fragment or variant of SEQ ID NO: 1 having pesticidal activity). Alternatively, a biologically active portion of a polypeptide of the invention can be identified by isolating a portion of a polynucleotide encoding said polypeptide (e.g., a portion of the polynucleotide of SEQ ID NO: 2), expressing the encoded polypeptide fragment (e.g., by recombinant expression in vitro), and assessing the pesticidal activity of the encoded portion of the protein. Polynucleotides that are fragments of a nucleotide sequence of the invention comprise at least about 50, about 100, about 150, about 200, about 250, about 300, about 350, about 400, about 450, about 500, about 550, about 600, or more contiguous nucleotides. A polynucleotide fragment that encodes a biologically active portion of a polypeptide of the invention will typically encode at least about 150, about 160, about 170, about 180 about 190, about 195, about 200, about 205, or more contiguous amino acids, or up to the total number of amino acids present in a full-length pesticidal protein of the invention.

Alternatively, fragments of a polynucleotide that are useful as hybridization probes generally do not encode polypeptide fragments retaining biological activity. Thus, fragments of a nucleotide sequence may range from at least about 20 nucleotides, about 50 nucleotides, about 100 nucleotides, and up to the full-length polynucleotide encoding the presently disclosed proteins.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites within the native polynucleotide; and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of SEQ ID NO: 1. Naturally occurring allelic variants can be identified with the use of well-known molecular biology techniques, including, for example, with polymerase chain reaction (PCR) and hybridization techniques as outlined elsewhere herein. Variant polynucleotides also include synthetically derived polynucleotides, such as those generated, for example, by using site-directed mutagenesis but which still encode a protein of the invention or a fragment thereof. Generally, variants of a particular polynucleotide of the invention will have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs and parameters described elsewhere herein. In certain embodiments, the variant polynucleotides do not have the nucleic acid sequence set forth in SEQ ID NO: 4. In other embodiments, the variant polynucleotides do not comprise the nucleic acid sequence set forth in SEQ ID NO: 4.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 1 or a fragment thereof (e.g., a biologically active fragment) are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 65%, about 70%, about 75%, about 80%, about 85%, about 90%, about 91%, about 92%, about 93%, about 94%, about 95%, about 96%, about 97%, about 98%, about 99% or more sequence identity. In other embodiments, the variant polynucleotides do not encode a polypeptide having the amino acid sequence set forth in SEQ ID NO: 3. In other embodiments, the variant polynucleotides do not encode a polypeptide that comprises the amino acid sequence set forth in SEQ ID NO: 3.

"Variant" polypeptide is intended to mean a protein derived from the native protein or a fragment thereof by deletion (so-called truncation) of one or more amino acids at the N-terminal and/or C-terminal end of the native protein; deletion or addition of one or more amino acids at one or more internal sites in the native protein; and/or substitution of one or more amino acids at one or more sites in the native protein. Variant polypeptides encompassed by the present invention are biologically active, that is they continue to possess a desired biological activity of the native protein. For example, in certain embodiments, polypeptide variants of the invention have pesticidal activity (e.g., nematicidal and/or insecticidal activity). Polypeptide variants of the invention may result from, for example, genetic polymorphism or from human manipulation. In general, biologically active variants of a polypeptide of the invention will have at least about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein, as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue. In certain embodiments, the variant polypeptides do not have the amino acid sequence set forth in SEQ ID NO: 3.

In other embodiments, the variant polypeptides do not comprise the amino acid sequence set forth in SEQ ID NO: 3.

The proteins of the invention may be altered in various ways including amino acid substitutions, deletions, truncations, and insertions. Methods for such manipulations are generally known in the art. For example, amino acid sequence variants and fragments of SEQ ID NO: 1 can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired biological activity (e.g., pesticidal activity). Obviously, the mutations that will be made in the DNA encoding the variant must not place the sequence out of reading frame and optimally will not create complementary regions that could produce secondary mRNA structure.

The deletions, insertions, and substitutions of the protein sequences encompassed herein are not expected to produce radical changes in the characteristics of the protein. Sequence variants likely to have conserved structure and function can be identified by conventional methods. For example, multi-sequence alignment tools can be used to identify invariant and conserved amino acids in protein domains having related structure. For example, additional twin-arginine translocation peptide-containing proteins having homology to SEQ ID NO: 1 have been identified, including sequences having GenBank Accession Numbers EEI90114.1 (SEQ ID NO: 3), EEI93150.1, ACU62846.1, ADY54317.1, ACU05835.1, ACY24875.1, ABG41197.1, AAK89062.2, EDM35643.1, and the like. Invariant and conserved amino acids in related proteins typically play important roles in determining the structure and/or function proteins. In general, invariant amino acids are neither deleted nor substituted in arriving at function variants of proteins. Conserved amino acids can be varied, typically by substitution with amino acids having side chains of similar size and/or chemical properties, but likewise should not be deleted. Invariant and/or conserved amino acids of SEQ ID NO: 1 include, e.g., amino acids located at positions 3-5, 7, 10, 11, 15, 47, 48, 50, 53, 55-57, 59, 61-65, 69, 73, 75, 79-81, 86, 93, 101, 106, 108, 115, 116, 119, 123, 126, 164, 166, 168-170, 172, 175-179, 181, 191-193, 195, 196, 204, and 208. In general, variation and or deletion of amino acids at positions that are neither invariant nor conserved in a multi-sequence alignment will typically result in functional variants.

Additionally, structural prediction tools such as CABS, ESyPred3D, HHpred, ROBETTA, and WHAT IF can be used to model the structure of protein domains based upon known crystal structures, allowing (1) the identification of amino acids located at the surface of a protein domain, and (2) in silico evaluation of the potential effects of introducing amino acid changes into a sequence. Non-conserved amino acids located at the surface of a protein domain are typically amenable to a range of different amino acid substitutions, whereas conserved amino acids located at the surface of a protein domain are often involved in important interactions (e.g., protein-protein, protein-carbohydrate, protein-lipid, etc.) and thus the types of permissible substitutions are more constrained (e.g., if substitutions are allowed, typically only conservative substitutions are permissible, although certain non-conservative substitutions may be permissible).

Accordingly, using conventional sequence analysis tools, structural prediction tools, and/or screening methods disclosed in the present application, polypeptide variants of the invention having conserved structure and function relative to SEQ ID NO: 1 can be identified and tested for function. Even when it is difficult to predict the exact effect of the substitution, deletion, or insertion in advance of doing so, one skilled in the art will appreciate that the effect can be evaluated by routine screening assays. That is, the activity can be evaluated by assays that measure pesticidal activity, such as nematicidal activity. See, e.g., Wei et al. (2003), Prot. Nat'l Acad. Sci. 100(5):2760-65.

Variant polynucleotides and proteins also encompass sequences and proteins derived from a mutagenic and recombinogenic procedure such as DNA shuffling. With such a procedure, one or more different pesticidal protein coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a gene encoding the nematicidal protein of SEQ ID NO: 1 and homologs thereof, such as, for example, the genes encoding the polypeptide sequences described in GenBank Accession Numbers EEI90114.1 (SEQ ID NO: 3), EEI93150.1, ACU62846.1, ADY54317.1, ACU05835.1, ACY24875.1, ABG41197.1, AAK89062.2, EDM35643.1, and the like, to obtain a new gene coding for a protein with an improved property of interest, such as increased pesticidal (e.g., nematicidal) activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other strains of *Sphingobacterium* and related microorganisms. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Functions of orthologs are often highly conserved among species. Thus, isolated polynucleotides that encode for a pesticidal (e.g., nematicidal) protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed, e.g., in Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and (d) "percentage of sequence identity."

(a) As used herein, a "reference sequence" is a defined sequence used as a basis for sequence comparison. A reference sequence may be a subset or the entirety of a specified sequence; for example, a segment of a full-length cDNA or gene sequence (e.g., a segment that encodes a protein structural domain), the complete cDNA or gene sequence, a segment of a full-length protein (e.g., a structural domain), or the full-length protein.

(b) As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two polynucleotides or polypeptides. For polynucleotides, the comparison window is typically at least 20 contiguous nucleotides in length, and optionally can be 30, 40, 50, 100, or longer. For polypeptides, a useful comparison window is either a length corresponding to the full-length protein or an active fragment thereof, such as a structural domain, a functionally conserved sequence, or a sequence involved in important binding interactions.

(c) As used herein, "sequence identity" or "identity" in the context of two polynucleotides or polypeptide sequences makes reference to the residues in the two sequences that are the same when aligned for maximum correspondence over a specified comparison window.

(d) As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL, ALIGN, GAP, BESTFIT, BLAST, PSI-BLAST, FASTA, and TFASTA. Alignments using these programs can be performed using the default parameters. For closely related sequences, alignment may also be performed manually by inspection.

The polynucleotides of the present invention can be expressed in a host cell, such as a bacterial, fungal, yeast, insect, mammalian, or preferably plant cells. By "host cell" is meant a cell which comprises a heterologous polynucleotide of the invention. Host cells may be prokaryotic cells, such as *E. coli*, or eukaryotic cells, such as yeast, insect, amphibian, or mammalian cells. In some embodiments, host cells are monocotyledonous or dicotyledonous plant cells.

The polynucleotides of the invention can be provided in expression cassettes for expression in a host cell. The expression cassettes of the invention find use in generating transformed plants, plant cells, and microorganisms and in practicing the methods for inducing pest resistance disclosed herein. The cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes a polypeptide (e.g., a pesticidal polypeptide of the invention) to be under the transcriptional regulation of the regulatory regions.

The expression cassette will include in the 5'-3' direction of transcription, a transcriptional and translational initiation region (i.e., a promoter), a polynucleotide of the invention, and a transcriptional and translational termination region (i.e., termination region) functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the host cell (e.g., plant or bacterial host), or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato proteinase inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. A wide range of plant promoters are discussed in the review of Potenza et al. (2004) *In Vitro Cell Dev Biol—Plant* 40:1-22, herein incorporated by reference. For example, the nucleic acids can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, such as a pest-inducible promoter. For example, the promoter can be a nematode-inducible promoter or a wound-inducible promoter. See, for example, U.S. Pat. No. 5,750,386 (nematode-inducible); potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Tissue-preferred promoters can be utilized to target enhanced expression of the pesticidal polypeptides of the invention within a particular plant tissue. For example, a tissue-preferred promoter may be used to express a polypeptide of the invention in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al.

(1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the sequences of the invention can be provided to a plant using a variety of transient transformation methods. Such transient transformation methods include, but are not limited to, the introduction of the protein or variants and fragments thereof directly into the plant or the introduction of a corresponding transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the pesticidal polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In certain embodiments, the polynucleotides of the present invention can be stacked with any combination of polynucleotide sequences of interest in order to create plants with a desired phenotype. For example, the polynucleotides of the present invention may be stacked with other pesticidal genes and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)); the disclosures of which are herein incorporated by reference.

The polynucleotides of the present invention can also be stacked with traits desirable for insect, disease, or herbicide resistance (e.g., *Bacillus thuringiensis* toxic proteins (U.S. Pat. Nos. 5,366,892; 5,747,450; 5,737,514; 5,723,756; 5,593, 881; Geiser et al. (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (e.g., the EPSPS gene and the GAT gene; see, for example U.S. Publication No. 20040082770 and WO 03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The present invention may be used to induce pest resistance or protect from pest attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In particular aspects, methods for inducing pest resistance in a plant comprise introducing into a plant at least one polynucleotide, wherein the polynucleotide comprises a nucleotide sequence encoding a pesticidal polypeptide of the invention. The polynucleotide is operably linked to a promoter that drives expression in the plant. The plant expresses the pesticidal polypeptide, thereby exposing the pest to the polypeptide at the site of attack. In particular embodiments, the polypeptides have nematicidal activity and the pest is a nematode. Expression of a polypeptide of the invention may be targeted to specific plant tissues where pest resistance is particularly important. Such tissue-preferred expression may be accomplished by, e.g., root-preferred, leaf-preferred, vascular tissue-preferred, stalk-preferred, or seed-preferred promoters. For nematode control, root-preferred promoters are typically optimal.

The compositions of the invention find further use in methods directed to protecting a plant from a pest or pathogen. "Protecting a plant from a pest or pathogen" is intended to mean killing the pest or pathogen or preventing or limiting disease formation on a plant. In some embodiments, a composition comprising a polypeptide of the invention and a carrier is applied directly to the environment of a plant pest or pathogen, such as, for example, on a plant or in the soil or other growth medium surrounding the roots of the plant, in order to protect the plant from pest and/or pathogen attack. Microorganisms comprising a polynucleotide encoding a polypeptide of the invention and methods of using them to protect a plant from a pest or pathogen are further provided. In some embodiments, the transformed microorganism is applied directly to a plant or to the soil in which a plant grows.

Biopesticide compositions, particularly nematicidal and insecticidal compositions, are thus encompassed by the present invention. Biopesticide compositions may comprise pesticidal polypeptides or microorganisms comprising a heterologous polynucleotide that encodes a pesticidal polypeptide of the invention. The biopesticide compositions of the invention may be applied to the environment of a plant pest or pathogen, as described herein below, thereby protecting a plant from pest and/or pathogen attack. Moreover, a biopesticide composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The biopesticide compositions find further use in the decontamination of plant pest and/or pathogens during the processing of grain for animal or human food consumption; during the processing of feedstuffs, and during the processing of plant material for silage. In this embodiment, the biopesticide compositions of the invention are presented to grain, plant material for silage, or a contaminated food crop, or during an appropriate stage of the processing procedure, in amounts effective for nematicidal and/or insecticidal activity.

A polynucleotide encoding a pesticidal, particularly nematicidal or insecticidal polypeptide of the invention may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the pesticidal protein.

Prokaryotic cells may be used as hosts for expression to create the biopesticide compositions. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235 and Mosbach et al. (1983) *Nature* 302:543-545).

Other suitable microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes*, fungi, particularly yeast, e.g., *Saccharomyces, Cryptococcus, Kluyveromyces, Sporobolomyces, Rhodotorula,* and *Aureobasidium.* Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

Other illustrative prokaryotes, both Gram-negative and gram-positive, include Enterobacteriaceae, such as *Escherichia, Erwinia, Shigella, Salmonella,* and *Proteus*; Bacillaceae; Rhizobiaceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces,* and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis,* and the like.

Polynucleotides encoding the pesticidal polypeptides of the invention can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Polynucleotides encoding the pesticidal polypeptides of the invention can be introduced into a root-colonizing *Bacillus cereus* by standard methods known in the art.

Polynucleotides encoding pesticidal polypeptides can be introduced, for example, into the root-colonizing *Bacillus* by means of electrotransformation. Specifically, polynucleotides encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein can, for example, be transformed into the root-colonizing *Bacillus* by means of electroporation (Lerecius et al. (1989) *FEMS Microbiol. Letts.* 60: 211-218).

Methods are provided for protecting a plant from a pest comprising applying an effective amount of a pesticidal polypeptide or biopesticide composition of the invention to the environment of the pest. "Effective amount" is intended to mean an amount of a protein or composition sufficient to control a pest. The pesticidal proteins and compositions can be applied to the environment of the pest by methods known to those of ordinary skill in the art.

Prior to the application of a biopesticide composition of the invention to an area of cultivation, the environment can be evaluated to determine if the pest of interest is present or if conditions are conducive to pest growth or infestation. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Evaluation of the environment can aid in determining the effective amount of the pesticidal polypeptide or biopesticde composition of the invention needed to control a pest within an area of cultivation.

Environmental conditions that can be evaluated include, but are not limited to, ground and surface water pollution concerns, intended use of the crop, crop tolerance, soil residuals, weeds present in area of cultivation, humidity, soil texture, pH of soil, amount of organic matter in soil, water content of soil, application equipment, and tillage practices. Following the evaluation of the environmental conditions, an effective amount of a pesticidal polypeptide or biopesticide composition of the invention can be applied to the crop, crop part, seed of the crop or area of cultivation.

The biopesticide compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins, more particularly nematicidal or insecticidal proteins, of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The biopesticide compositions of the present invention can be in a suitable form for direct application or as a concentrate of primary composition that requires dilution with a suitable quantity of water or other dilutent before application. The concentration of the pesticidal polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

The biopesticide compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pests as a protective measure. For example, the pesticidal protein and/or transformed microorganisms of the invention may be mixed with grain to protect the grain during storage. It is generally important to obtain good control of pests in the early stages of plant growth, as this is the time when the plant can be most severely damaged. In one embodiment of the invention, the composition is applied directly to the soil, at a time of planting, in granular form of a composition of a carrier and pesticidal polypeptides or transformed microorganisms of the invention. Another embodiment is a granular form of a composition comprising an agrochemical such as, for example, a herbicide, an insecticide, a fertilizer, an inert carrier, and pesticidal polypeptides or transformed microorganisms of the invention.

One of skill in the art will appreciate that the compositions and methods disclosed herein can be used with other compositions and methods available in the art for protecting plants from pathogen attack. For example, methods of the invention can comprise the use of one or more herbicides, insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. General references for these agricultural protectants include The Pesticide Manual, 13th Edition, C. D. S. Tomlin, Ed., British Crop Protection Council, Farnham, Surrey, U.K., 2003 and The BioPesticide Manual, 2nd Edition, L. G. Copping, Ed., British Crop Protection Council, Farnham, Surrey, U.K., 2001.

The embodiments of the present invention may be effective against a variety of plant pathogens. Pathogens of the invention include, but are not limited to, nematodes, insects, viruses or viroids, bacteria, fungi, and the like. Nematodes include plant parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp. Plant parasitic nematodes include those in the genre *Aphelenchoides, Ditylenchus, Globodera, Heterodera, Longidorus, Meloidogyne, Nacobleus, Pratylenchus, Trichodorus* and *Xiphinema.*

In an embodiment of the invention, the compositions of the invention may be used as a pharmaceutical composition for treatment of parasites (e.g., nematode parasites) in humans and other animals. Examples of nematode parasites include, but are not limited to, ascarids (*Ascaris*), filarias (e.g., *Onchocerca volvulus*), hookworms, pinworms (*Enterobius*), whipworms (e.g., *Trichuris trichiura*), *Trichinella spiralis, Baylisascaris, Dirofilaria immitis, Haemonchus contortus, Nippostrongylus brasiliensis, Ancylostoma duodenale,* and *Necator americanus.* In some of these embodiments, the pesticidal polypeptide is combined with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

The presently disclosed pharmaceutical compositions may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the polypeptides and pharmaceutical compositions of the invention.

The polypeptides of the invention can be used for any application including coating surfaces to target parasites. In this manner, target parasites include parasitic nematodes that infect humans and animals (e.g., domestic livestock). Surfaces that might be coated with the pesticidal compositions of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The articles "a" and "an" are used herein to refer to one or more than one (i.e., to at least one) of the grammatical object of the article. By way of example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXAMPLES

Example 1

C. elegans Feeding Assay and Identification of Strain 75G5

The 75G5 strain was obtained from a biodiverse collection of bacterial strains. The strain was grown in Tryptic soy medium overnight at 20° C., with shaking at 225 rpm. 5 to 30 µL of the liquid culture was added into assay wells in 96-well plates. Each assay well contained 120 µL of liquid with ~50 L1 staged C. elegans, 30 µg/mL tetracycline, 30 µg/mL chloramphenicol, and S-medium. E. coli strain OP50 was used as a negative control. Forty-eight hours later, the assay plates were scored under a microscope by checking the worm's growth and development. The 75G5 culture totally inhibited worm development and all worms were arrested at the L1 stage, indicating that the 75G5 strain shows nematicidal activity.

To further characterize the nematicidal activity, the 75G5 strain was cultured in 50 ml Tryptic soy medium at 20° C. for 18 h, with 225 rpm shaking. The cell pellet was collected after centrifugation at 700 rpm and then stored at −80 C. Total protein was extracted from the cell pellet using the B-PER II Bacterial Protein Extraction Reagent from Thermo. The lysate was centrifuged twice at 10,000 rpm and the final supernatant was collected as the total protein sample. The total protein sample was tested in the C. elegans feeding assay, as described above, and displayed strong nematicidal activity, arresting worms at the L1 stage. When the total protein sample was treated with proteinase K and high temperature, its antinematode activity was lost. This indicates that the nematicidal activity is proteinaceous.

Genomic DNA was subsequently extracted from the 75G5 strain and specific PCR primers for rDNA were used to isolate ~1400 bp rDNA sequence from 75G5. Blast search of the 1400 bp sequence revealed that 75G5 is a *Sphingobacterium spiritivoru* strain.

Example 2

Separation and Identification of a Nematicidal Toxin from Sphingobacterium spiritivorum Strain 75G5

Strain 75G5 was grown in tryptic soy medium for 16 to 18 hours at 20° C. Cells were harvested by centrifugation and washed with phosphate buffered saline. All subsequent steps were performed at 4° C. unless noted otherwise. Washed cells from 1 liter of medium were resupended in 120 ml of 20 mM Tris-HCl buffer, pH 7.6, and passed twice through a French Pressure cell at 10000 psi. The resulting lysate was clarified by centrifugation at 1000 g for 20 minutes. The supernatant was then further subjected to ultracentrifugation at 200,000 g for 1 hour to isolate insoluble membrane fractions at the bottom of the tube. The supernatant was discarded and membrane associated proteins were solubilized with B-PER II (Thermo Scientific), containing 20 mM Tris-HCl, pH7.6. Ultracentrifugation was repeated and soluble membrane associated proteins were subjected to fractionation by anion exchange chromatography, performed at room temperature. About 10 to 20 mg of soluble protein were injected onto a Mono Q 5/50 GL column (1 ml, GE Healthcare) equilibrated with Buffer A: B-PER II diluted 4-fold with 20 mM Tris-HCl pH 8.0. Unbound protein was washed out with buffer A and protein containing nematicidal activity was eluted with a linear 30 ml gradient to buffer B: B-PER II diluted 4-fold with 20 mM Tris-HCl pH 8.0, 0.75M NaCl. Active fractions were pooled and dialyzed against Buffer C: BPER-II, diluted 4-fold in 20 mM sodium acetate, pH 5, using a 10,000 molecular weight cutoff membrane. Further purification was achieved by injection of the dialized pool onto a 1 ml Mono S 5/50 GL column (GE Healthcare) equilibrated with buffer C. A linear, 20 ml gradient was run at 2.55 cm/min with buffer C, containing 750 mM NaCl.

Eluting fractions were assayed for nematicidal activity and pooled. SDS-PAGE analysis showed two protein bands after staining with silver, with molecular weights of approximately 25 and 75 kDa, respectively. N-terminal sequence information obtained by Edman degradation was searched using BLAST for protein identification. The large and inactive 75 kDa protein was identified as an oxidoreductase with high homology to an oxidoreductase from *Sphingobacterium spiritivorum*, accession number gi227240101. The small and active 25 kDa protein, which was designated as RX025, was subjected to tryptic digestion and LC/MS/MS analysis, followed by NCBI database search using Mascot (Matrixscience). A single tryptic peptide (K)FDGNYPYKK matched a putative twin arginine translocation pathway signal protein from *Sphingobacterium spiritivorum*, ATCC33300, accession number gi 227240099. In-gel digest LC/MS/MS spectra were further analyzed using PEAKS software (Bioinformatics Solutions Inc) for de novo sequencing and subsequent homology searching. Four additional internal peptides were identified with high homology to gi 227240099, increasing confidence of correct identification.

Example 3

Cloning and Testing Twin-Arginine Translocation Peptide

Since strain 75G5 showed closely homology to *Sphingobacterium spiritivorum*, ATCC33300 strain, based on rDNA sequences and peptide sequence obtained from the RX025 protein, the *Sphingobacterium spiritivorum* ATCC33300 strain was ordered from the ATCC (American Type Culture Collection). Total protein extracted from the ATCC strain showed similar nematicidal activity as compared to strain 75G5.

To obtain the gene sequence of the RX025 protein, total genomic DNA was isolated from strain ATCC33300 using the Sigma Bacterial DNA Extraction Kit. Primers were designed based on the peptide information obtained from Mass Spectrometery. The primers had the following sequences:

```
5' primer:
                                        (SEQ ID NO: 5)
aagcatgcatagaagagaagcattacagcgtg 3' primer:
                                        (SEQ ID NO: 6)
taggatccttatgcccaggcgtgctctcctttttataaggataattac
```

Using these primers, the RX025 gene was amplified by PCR from the ATCC33300 genomic DNA sample. Upon sequences, the PCR product was found to have the following sequence (from 5' to 3'):

```
                                                                        (SEQ ID NO: 7)
gcatgcatagaagagaagcattacagcgtgtcgccctgttgatgggaggaactgtcattggcgctaatcttttc ctggaaggctgttcacgttcagcttcaaaagatacagcaaaactttttgaaaaagattcggtcaattttcttggc
```

-continued

```
gatctggcagaagcgatcttgcccaaaacaagtacaccgggagcgaaggaagcaggcgtaggagaattt atccctgtcatgatcagagactgttatgcagacactgagcaaaaggtattcttagacggaatcaatactgttga tgaacgtgctaagaaggaattcggtaagaagtttcaggaactaagtaaggaagatcagactaaatttgtcaa tattcttgataaagaagccagtgaatacaacgctaagcaggcagaagctacaaaagcacagcgtgaaaa ggatgcattgaaacaaaatgaaatgtatcgtgtgccgaaaagcgatccgccacactggttcacgatgttcaa gcaattgacccttacaggtttcttacttcagaactgggcgctactaaagcgctacgttatgtgaaaattccggg gaaatttgatggtaattatccttataaaaaaggagagcacgcctgggcataaggatcc.
```

The open reading frame and the corresponding protein sequence are set forth in FIGS. 1b and 1a, respectively.

To verify that the RX025 gene is causally related to the nematicidal activity exhibited by the 75G5 *Sphingobacterium spiritivorum* ATCC33300 strain, the RX025 gene was cloned from ATCC33300 (*Sphingobacterium spiritivorum*) strain into *E. coli* expression vectors pMAL (MBP fusion) and pQE80L. The expression constructs were then transformed into *E. coli* TOP10 strain with carbenicillin selection. For protein expression, an *E. coli* overnight culture was diluted by 50 fold and grown at 37° C. for 2.5 hours (to $OD_{600}$ ~0.5). Protein expression was induced by adding 0.8 mM IPTG and the culture was grown for another 5 hours at 30° C. After induction, 20 ul of *E. coli* cells were used for running SDS gel to check protein expression, as shown in FIG. 3. *E. coli* strains expressing the RX025 protein were then tested for nematicidal activity using the *C. elegans* feeding assay described in Example 1. Consistent with the RX025 gene being causally related to nematicidal activity, *E. coli* strains that expressed the RX025 gene inhibited worm development, arresting worms at the L1 stage.

Example 4

Variant Polynucleotides and Polypeptides of the Invention

A. Polynucleotide Variants

The nucleotide sequence set forth in SEQ ID NO: 2 is used to generate variant nucleotide sequences having the nucleotide sequence of the open reading frame with about 70%, 76%, 81%, 86%, 92%, and 97% nucleotide sequence identity when compared to the starting unaltered ORF nucleotide sequence of SEQ ID NO: 2. These functional variants are generated using a standard codon table. While the nucleotide sequence of the variant is altered, the amino acid sequence encoded by the open reading frame does not change.

B. Variant Amino Acid Sequences

Variant amino acid sequences of SEQ ID NO: 1 are generated. In this example, one amino acid is altered. Specifically, the open reading frame set forth in SEQ ID NO: 2 is reviewed to determined the appropriate amino acid alteration. The selection of the amino acid to change is made by consulting a protein alignment (e.g., with polypeptide sequences described in GenBank Accession Numbers EEI90114.1 (SEQ ID NO: 3), EEI93150.1, ACU62846.1, ADY54317.1, ACU05835.1, ACY24875.1, ABG41197.1, AAK89062.2, EDM35643.1, or the like). An amino acid is selected that is deemed not to be under high selection pressure (not highly conserved) and which is rather easily substituted by an amino acid with similar chemical characteristics (i.e., similar functional side-chain). Using the protein alignment an appropriate amino acid can be changed. Once the targeted amino acid is identified, the procedure outlined in Example 4A is followed. Variants having about 70%, 75%, 81%, 86%, 92%, and 97% nucleic acid sequence identity to SEQ ID NO: 2 are generated using this method.

C. Additional Amino Acid Sequence Variants

In this example, artificial protein sequences are created having 82%, 87%, 92%, and 97% identity relative to the reference protein sequence (SEQ ID NO: 1). This latter effort requires identifying conserved and variable regions and then the judicious application of an amino acid substitutions table. These parts will be discussed in more detail below.

The determination of which amino acid sequences are altered is made largely based on the conserved domains and the extent to which amino acid residues in those domains tend to be conserved between homologous sequences. Based on sequence alignments, the various regions of SEQ ID NO: 1 that can likely be altered are identified. Typically, conservative substitutions can be made in conserved regions without altering function. In addition, one of skill will understand that functional variants of the polypeptides of the invention can have minor non-conserved amino acid alterations in the conserved domain.

The conserved regions of SEQ ID NO: 1 are found between about amino acid 1 to about amino acid 20 (N terminus), about amino acid 47 to about amino acid 126 (central domain), and about amino acid 164 to about amino acid 208 (C terminus).

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 1.

TABLE 1

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |

TABLE 1-continued

Substitution Table

| Amino Acid | Strongly Similar and Optimal Substitution | Rank of Order to Change | Comment |
|---|---|---|---|
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution (e.g., residues deemed to be invariant are not changed). The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

The variant amino acid sequences are written as output. Perl script is used to calculate the percent identities. Using this procedure, variants are generating having about 82%, 87%, 92%, and 97% amino acid identity to the starting unaltered ORF nucleotide sequence of SEQ ID NO: 1.

Example 5

Transformation of Soybean Root Cultures and Testing of Soybean Cyst Nematode (SCN) Resistance

*Agrobacterium rhizogenes* strain K599 was used for soybean hairy root transformation, and the gene function and promoter activity were analyzed in transgenic soybean hairy roots. Stocks of *A. rhizogenes* were maintained on minimal A media (see recipes, below). Plasmid DNA was introduced into *A. rhizogenes* strain K599 using the freeze-thaw method, as described in Ha (1988) Plant Molecular Manual, eds. Gelvin, Schilperoort, and Verma, pp. A3/1-A3/7.

Soybean seeds were surface-sterilized with chlorine gas at room temperature for 12-16 hours. The seeds were then aerated in a clean air hood for at least 30 minutes. Seeds were germinated and cultured in Magenta™ boxes (Magenta Corporation) containing sterile potting soil with 10 to 15 mL of 25% Gamborg's B-5 Basal medium with minimal organics (G5893, Sigma). The boxes were placed under a mix of fluorescent and incandescent lights providing a 16-hour day/8-hour night cycle and constant temperature of about 26° C. Six-day-old seedlings of non-transformed plants were inoculated with a freshly grown culture of *A. rhizogenes* previously transformed with DNA constructs. The transformed *A. rhizogenes* was introduced into the hypocotyls just under the cotyledons by wounding 4 to 6 times in the epidermal cell layer with a 23-gauge needle containing the *A. rhizogenes*. The inoculated plants were cultured under the same conditions as those described above for seed germination.

After the soybean hypocotyls were inoculated with *A. rhizogenes*, adventitious soybean roots developed and were excised. Initially these putative transformed roots were cultured in liquid B-5 medium with antibiotics to cure the roots of any bacteria; antibiotics included 500 mg/L cefotaxime (Calbiochem-Novabiochem, La Jolla, Calif.) and 200 mg/L vancomycin (Spectrum Quality Products, Los Angeles, Calif.). Roots were transferred to fresh liquid medium every 2-3 days; this transfer to fresh media is performed a total of three times. After the third transfer, each root was moved to a plate of MXB medium with Gelrite™ gelling agent. To determine whether roots were transformed, a 1-2 cm root piece was placed in a 1.5 mL tube with GUS staining solution (0.05% X-Gluc in 100 mM sodium phosphate buffer at pH 7.0 containing 10 MM EDTA, 0.1% Triton, and 0.5 mM K4Fe (CN)-61420). Roots were incubated in this solution for 2 to 4 hours at 27 to 29° C.; solutions were then evaluated for development of the blue color indicative of GUS activity. Roots testing positive by this assay and control roots that were not transformed were cultured in MXB medium with Gelrite™ gelling agent in an incubator without light at 26 to 30° C. A 1-4 cm piece of root tip was excised and transferred to fresh medium every 2-4 weeks.

Roots testing positive for transformation with the DNA construct were assayed for resistance to infection by soybean cyst nematodes (SCN). Roots were transferred to 6-well plates containing NM medium with Daishin agar. After 4-10 days, roots were inoculated with second-stage SCN juveniles. Two to five root tips were placed in each well of a 6-well culture dish; four of the wells contained roots transformed with *A. rhizogenes* containing the RX008 construct and the other two wells contained control roots transformed with *A. rhizogenes* lacking the RX008 construct. One sample of control roots in this assay was an SCN-compatible control root sample from an SCN-susceptible or "compatible" soybean genotype such as Pioneer brand 9204. The other sample of control roots was an SCN-resistant soybean genotype such as Jack and is thus an SCN-resistant or "incompatible" control sample. Roots were inoculated by placing 500 second-stage SCN race 3 juveniles directly onto the roots in each well and incubating for 7 days at 26 to 28° C.

The following stock solutions and media are used for transformation and regeneration of soybean roots:

Stock Solutions (per Liter):

B-5 Majors: 25.00 g KNO3, 1.34 g (NH4) 2SO4, 2.50 g MgSO4-7H2O, 1.50 g CaCl2-2H2O, 1.31 g NaH2PO4 (anhydrous).

B-5 Minors: 1.00 g MnSO4-H2O, 0.30 g H3BO3, 0.20 g ZnSO4-7H2O, 0.075 g KI.

B-5 Vitamin Stock with Thiamine: 1 L Vitamin B-5 Stock, 1 g Thiamine HCl.

Iron Mix: 3.73 g. Na2EDTA, 2.78 g FeSO4-7H2O.

Media (per Liter):

Minimal A medium: 10.5 g K2HPO4, 4.5 g KH2PO4, 1.0 g (NH4)2SO4, 0.5 g (Na)2C6HSO7-2H2O, 1 mL 1.0 M MgSO4-7H2O, 10 mL 20% w/v sucrose, 15 g agar, B-5 medium: 0.6 g MES (2-(N-Morpholino) ethane-sulfonic acid (M5287, Sigma)), 20 g sucrose, 10 mL B-5 minors, 100 mL B-5 majors, 10 mL B-5 Vitamin Stock with Thiamine, 10 mL Iron mix.

MXB medium: Murashige and Skoog Basal nutrient salts (M5524, Sigma), 10 mL Vitamin B-5 Stock with Thiamine, 30 g sucrose.

MXB medium with Gelrite™: add 3 g Gelrite gelling agent to 1 L MXB medium, pH 5.7.

MXB medium with Daishin agar: add 8 g Daishin agar to 1 L MXB medium, pH 6.5.

Six weeks after SCN inoculation, the cyst numbers were counted from each plate and the data was analyzed. In these hairy root assays, expression of the RX008 construct resulted in a 22% reduction number of cysts, as compared to the empty vector control (see FIG. 4). For expression in soybean cells, the RX008 sequence was optimized based on soy codon usage and a BAA signal was add to the N-terminal of the gene. The BAA-RX008 construct (SEQ ID NO:6) was transformed into soybean hairy roots as described above.

Example 6

Transformation of Soybean Embryos

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying a protein coding sequence (e.g., encoding a polypeptide of the invention) are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the protein coding sequence are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for nematode and/or insect resistance.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. An isolated polypeptide comprising
    the amino acid sequence set forth in SEQ ID NO: 1
    and wherein said polypeptide has nematicidal activity.

2. An expression cassette comprising a polynucleotide comprising a nucleotide sequence operably linked to a heterologous promoter, wherein the nucleotide sequence is selected from the group consisting of:
    (a) the nucleotide sequence set forth in SEQ ID NO: 2; and
    (b) a nucleotide sequence encoding an amino acid sequence comprising SEQ ID NO: 1, and wherein said polynucleotide encodes a polypeptide having nematicidal activity.

3. The expression cassette of claim 2, wherein the promoter is one that drives expression in a plant.

4. A plant comprising a heterologous polynucleotide operably linked to a promoter that drives expression in the plant, wherein said heterologous polynucleotide comprises a nucleotide sequence selected from the group consisting of:
    (a) the nucleotide sequence set forth in SEQ ID NO: 2; and
    (b) a nucleotide sequence encoding an amino acid sequence comprising SEQ ID NO: 1,
    wherein said heterologous polynucleotide encodes a polypeptide having nematicidal activity.

5. The plant of claim 4, wherein said plant is a cell.

6. The plant of claim 4, wherein said plant is a monocot.

7. The plant of claim 6, wherein said monocot is maize, sugarcane, wheat, rice, barley, sorghum, or rye.

8. The plant of claim 4, wherein said plant is a dicot.

9. The plant of claim 8, wherein the dicot is soybean, Brassica, sunflower, cotton, alfalfa, or tomato.

10. The plant of any one of claims 4 to 9, wherein said heterologous polynucleotide is stably incorporated into the genome of the plant.

11. The plant of claim 10, wherein said plant is a seed.

12. A method of increasing the level of a polypeptide in a plant comprising introducing into said plant a heterologous polynucleotide comprising a nucleotide sequence selected from the group consisting of:
    (a) the nucleotide sequence set forth in SEQ ID NO: 2; and
    (b) a nucleotide sequence encoding an amino acid sequence comprising SEQ ID NO: 1,
    wherein said heterologous polynucleotide encodes a polypeptide having nematicidal activity.

13. The method of claim 12, wherein said heterologous polynucleotide is stably integrated into the genome of the plant.

14. The method of claim 12 or 13, wherein said plant is a plant cell.

15. The method of claim 13, wherein said plant is a seed.

16. The method of claim 12 or 13, wherein said plant is a dicot.

17. The method of claim 16, wherein said dicot is soybean, Brassica, sunflower, cotton, alfalfa or tomato.

18. The method of claim 12 or 13, wherein said plant is a monocot.

19. The method of claim 18, wherein said monocot is maize, sugarcane, wheat, rice, barley, sorghum, or rye.

* * * * *

SEQUENCE LISTING

```
<160> NUMBER OF SEQ ID NOS: 7

<210> SEQ ID NO 1
<211> LENGTH: 209
<212> TYPE: PRT
<213> ORGANISM: Sphingobacterium spiritivorum

<400> SEQUENCE: 1

Met His Arg Arg Glu Ala Leu Gln Arg Val Ala Leu Leu Met Gly Gly
1               5                   10                  15

Thr Val Ile Gly Ala Asn Leu Phe Leu Glu Gly Cys Ser Arg Ser Ala
            20                  25                  30

Ser Lys Asp Thr Ala Lys Leu Phe Glu Lys Asp Ser Val Asn Phe Leu
        35                  40                  45

Gly Asp Leu Ala Glu Ala Ile Leu Pro Lys Thr Ser Thr Pro Gly Ala
    50                  55                  60

Lys Glu Ala Gly Val Gly Glu Phe Ile Pro Val Met Ile Arg Asp Cys
65                  70                  75                  80

Tyr Ala Asp Thr Glu Gln Lys Val Phe Leu Asp Gly Ile Asn Thr Val
                85                  90                  95
```

```
Asp Glu Arg Ala Lys Lys Glu Phe Gly Lys Lys Phe Gln Glu Leu Ser
                100                 105                 110
Lys Glu Asp Gln Thr Lys Phe Val Asn Ile Leu Asp Lys Glu Ala Ser
            115                 120                 125
Glu Tyr Asn Ala Lys Gln Ala Glu Ala Thr Lys Ala Gln Arg Glu Lys
        130                 135                 140
Asp Ala Leu Lys Gln Asn Glu Met Tyr Arg Val Pro Lys Ser Asp Pro
145                 150                 155                 160
Pro His Trp Phe Thr Met Phe Lys Gln Leu Thr Leu Thr Gly Phe Phe
                165                 170                 175
Thr Ser Glu Leu Gly Ala Thr Lys Ala Leu Arg Tyr Val Lys Ile Pro
            180                 185                 190
Gly Lys Phe Asp Gly Asn Tyr Pro Tyr Lys Lys Gly His Ala Trp
        195                 200                 205
Ala

<210> SEQ ID NO 2
<211> LENGTH: 630
<212> TYPE: DNA
<213> ORGANISM: Sphingobacterium spiritivorum

<400> SEQUENCE: 2
atgcatagaa gagaagcatt acagcgtgtc gccctgttga tgggaggaac tgtcattggc      60
gctaatcttt tcctggaagg ctgttcacgt tcagcttcaa agatacagc aaaacttttt     120 gaaaagatt cggtcaattt tcttggcgat ctggcagaag cgatcttgcc caaaacaagt     180
acaccgggag cgaaggaagc aggcgtagga gaatttatcc ctgtcatgat cagagactgt     240
tatgcagaca ctgagcaaaa ggtattctta gacggaatca atactgttga tgaacgtgct     300
aagaaggaat tcggtaagaa gtttcaggaa ctaagtaagg aagatcagac taaatttgtc     360
aatattcttg ataaagaagc cagtgaatac aacgctaagc aggcagaagc tacaaaagca     420
cagcgtgaaa aggatgcatt gaaacaaaat gaaatgtatc gtgtgccgaa agcgatccg      480 ccacactggt tcacgatgtt caagcaattg acccttacag gtttctttac ttcagaactg     540
ggcgctacta aagcgctacg ttatgtgaaa attccgggga aatttgatgg taattatcct     600
tataaaaaag gagagcacgc ctgggcataa                                      630

<210> SEQ ID NO 3
<211> LENGTH: 209
<212> TYPE: PRT
<213> ORGANISM: Sphingobacterium spiritivorum

<400> SEQUENCE: 3

Met Asn Arg Arg Glu Ala Leu Gln Arg Val Ala Leu Leu Met Gly Gly
 1               5                  10                  15
Thr Val Ile Gly Ala Asn Leu Phe Leu Glu Gly Cys Ser Arg Ser Ala
                20                  25                  30
Ser Lys Asp Thr Ala Lys Leu Phe Glu Lys Asp Ser Val Asn Phe Leu
            35                  40                  45
Gly Asp Leu Ala Glu Ala Ile Leu Pro Lys Thr Ser Thr Pro Gly Ala
        50                  55                  60
Lys Glu Ala Gly Val Gly Glu Phe Ile Pro Val Met Ile Arg Asp Cys
65                  70                  75                  80
Tyr Ala Asp Thr Glu Gln Lys Val Phe Leu Asp Gly Ile Asn Thr Val
                85                  90                  95
```

```
Asp Glu Arg Ala Lys Lys Glu Phe Gly Lys Lys Phe Gln Glu Leu Ser
                100                 105                 110

Lys Glu Asp Gln Thr Lys Phe Val Asn Ile Leu Asp Lys Glu Ala Ser
            115                 120                 125

Glu Tyr Asn Ala Lys Gln Ala Glu Ala Thr Lys Ala Gln Arg Glu Lys
        130                 135                 140

Asp Ala Leu Lys Gln Asn Glu Met Tyr Arg Val Pro Lys Ser Asp Pro
145                 150                 155                 160

Pro His Trp Phe Thr Met Phe Lys Gln Leu Thr Leu Thr Gly Phe Phe
                165                 170                 175

Thr Ser Glu Leu Gly Ala Thr Lys Ala Leu Arg Tyr Val Lys Ile Pro
            180                 185                 190

Gly Lys Phe Asp Gly Asn Tyr Pro Tyr Lys Lys Gly Glu His Ala Trp
        195                 200                 205

Ala
```

<210> SEQ ID NO 4
<211> LENGTH: 628
<212> TYPE: DNA
<213> ORGANISM: Sphingobacterium spiritivorum

<400> SEQUENCE: 4

```
atgaatagaa gagaagcatt acagcgtgtc gccctgttga tgggaggaac tgtcattggc    60
gctaatcttt tcctggaagg ctgttcacgt tcagcttcaa agatacagc aaaactttt   120
gaaaaagatt cggtcaattt tcttggcgat ctggcagaag cgatcttgcc caaaacaagt   180
acaccgggag cgaaggaagc aggcgtagga gaatttatcc ctgtcatgat cagagactgt   240
tatgcagaca ctgagcaaaa ggtattctta gacggaatca atactgttga tgaacgtgct   300
aagaaggaat tcggtaagaa gtttcaggaa ctaagtaagg aagatcagac taaatttgtc   360
aatattcttg ataaagaagc cagtgaatac aacgctaagc aggcagaagc tacaaaagca   420
cagcgtgaaa aggatgcatt gaaacaaaat gaaatgtatc gtgtgccgaa aagcgatccg   480
ccacactggt tcacgatgtt caagcaattg acccttacag gtttctttac ttcagaactg   540
ggcgctacta aagcgctacg ttatgtgaaa attccgggga aatttgatgg taattatcct   600
tataaaaaag gagagcacgc ctgggcat                                      628
```

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5

```
aagcatgcat agaagagaag cattacagcg tg                                  32
```

<210> SEQ ID NO 6
<211> LENGTH: 49
<212> TYPE: DNA
<213> ORGANISM: Artificial Sequence
<220> FEATURE:
<223> OTHER INFORMATION: Primer

<400> SEQUENCE: 6

```
taggatcctt atgcccaggc gtgctctcct tttttataag gataattac                49
```

<210> SEQ ID NO 7
<211> LENGTH: 638

```
<212> TYPE: DNA
<213> ORGANISM: Artificial Sequence
<220> FEATURE:
<223> OTHER INFORMATION: Sequence of PCR Product Obtained by Amplifying
      the RX025 gene

<400> SEQUENCE: 7
gcatgcatag aagagaagca ttacagcgtg tcgccctgtt gatgggagga actgtcattg      60
gcgctaatct tttcctggaa ggctgttcac gttcagcttc aaaagataca gcaaaacttt     120
ttgaaaaaga ttcggtcaat tttcttggcg atctggcaga agcgatcttg cccaaaacaa     180
gtacaccggg agcgaaggaa gcaggcgtag gagaatttat ccctgtcatg atcagagact     240
gttatgcaga cactgagcaa aaggtattct tagacggaat caatactgtt gatgaacgtg     300
ctaagaagga attcggtaag aagtttcagg aactaagtaa ggaagatcag actaaatttg     360
tcaatattct tgataaagaa gccagtgaat acaacgctaa gcaggcagaa gctacaaaag     420
cacagcgtga aaaggatgca ttgaaacaaa atgaaatgta tcgtgtgccg aaaagcgatc     480
cgccacactg gttcacgatg ttcaagcaat tgacccttac aggtttcttt acttcagaac     540
tgggcgctac taaagcgcta cgttatgtga aaattccggg gaaatttgat ggtaattatc     600
cttataaaaa aggagagcac gcctgggcat aaggatcc                             638
```